US00PP34627P3

(12) United States Plant Patent
Perrault et al.

(10) Patent No.: US PP34,627 P3
(45) Date of Patent: Oct. 4, 2022

(54) HOP PLANT NAMED 'ADHA 1940'

(50) Latin Name: *Humulus lupulus*
Varietal Denomination: ADHA 1940

(71) Applicant: ASSOCIATION FOR THE DEVELOPMENT OF HOP AGRONOMY LLC, Moxee, WA (US)

(72) Inventors: Jason Perrault, Toppenish, WA (US); Eugene G. Probasco, Yakima, WA (US); James F. Boyd, Nevada City, CA (US)

(73) Assignee: Association for the Development of Hop Agronomy LLC, Moxee, WA (US)

( * ) Notice: Subject to any disclaimer, the term of this patent is extended or adjusted under 35 U.S.C. 154(b) by 0 days.

(21) Appl. No.: 16/974,326

(22) Filed: Dec. 28, 2020

(65) Prior Publication Data

US 2021/0243929 P1 Aug. 5, 2021

Related U.S. Application Data

(60) Provisional application No. 62/974,939, filed on Dec. 31, 2019.

(51) Int. Cl.
*A01H 5/02* (2018.01)
*A01H 6/28* (2018.01)
*A01H 6/00* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ... A01H 5/08; A01H 5/02; A01H 5/00; A01H 6/28; A01H 6/00
See application file for complete search history.

*Primary Examiner* — June Hwu
(74) *Attorney, Agent, or Firm* — Svendsen Legal, LLC

(57) ABSTRACT

A new hop plant named 'ADHA 1940' is disclosed. 'ADHA 1940' is used in brewing for its unique noble-like aromatic qualities.

5 Drawing Sheets

Genus and species: *Humulus lupulus*.
Variety denomination: 'ADHA 1940'.

STATEMENT REGARDING FEDERALLY SPONSORED RESEARCH OR DEVELOPMENT

None

BACKGROUND OF THE INVENTION

'ADHA 1940' is a product of a controlled breeding program carried out by the inventor in the Yakima Valley of Washington State. 'ADHA 1940' was one of several seedlings resulting from a cross made in 2011 with female parent 'Summit' (U.S. Plant Pat. No. 18,039), and pollen from male parent 'ADHA 34/95/57' (not patented). A single plant of 'ADHA 1940' was planted in Toppenish, Wash. in 2012, then moved to the Moxee, Wash. area in 2013. 'ADHA 1940' was observed and evaluated over several years, and expanded through asexual propagation in 2016 via softwood cuttings, to a large-scale test plot in the Moxee, Wash. area for further evaluation. Throughout several generations of asexual propagation, 'ADHA 1940' has been observed to retain its distinctive characteristics and has remained true to type.

BRIEF DESCRIPTION OF THE PHOTOGRAPHS

Figure 1:
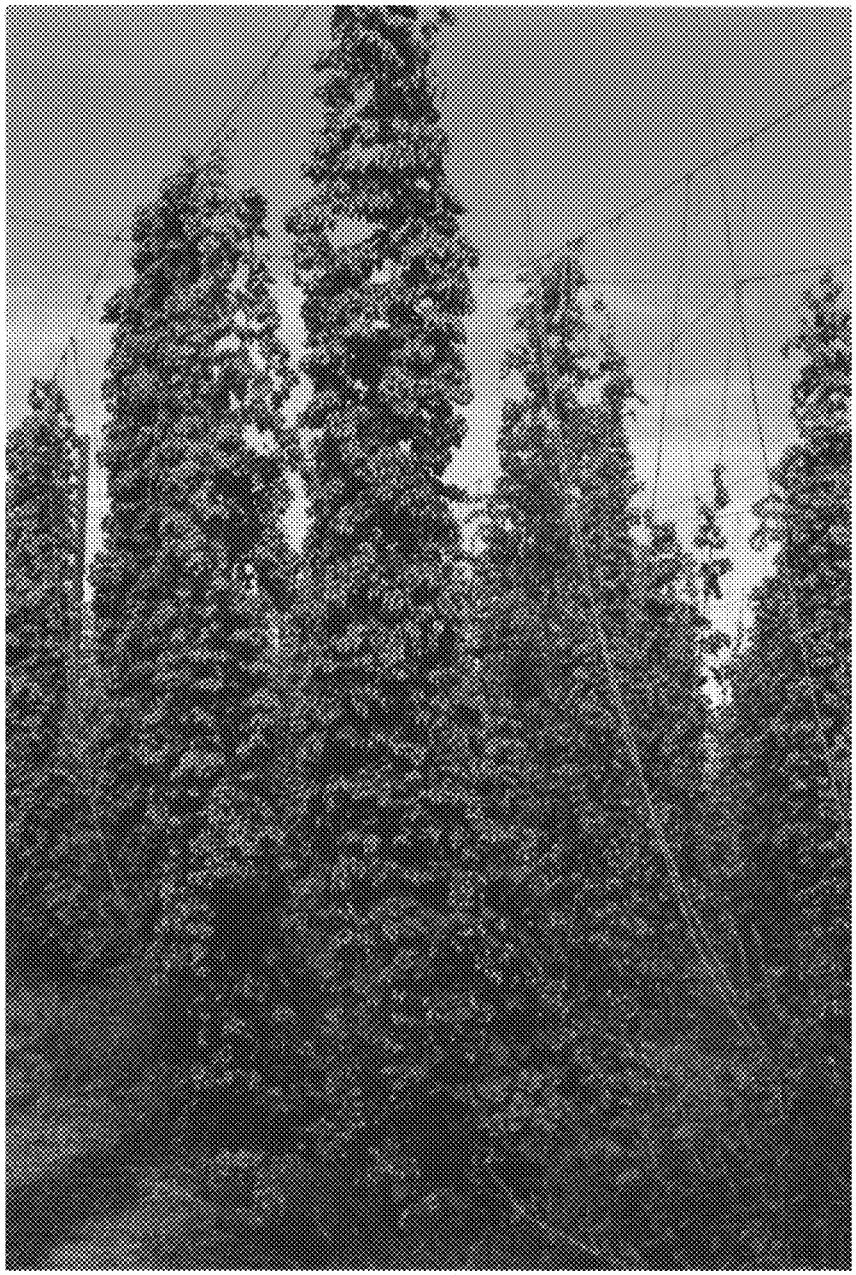
FIG. 1 illustrates mature 'ADHA 1940' hop plants, grown on a trellis.
Figure 2:
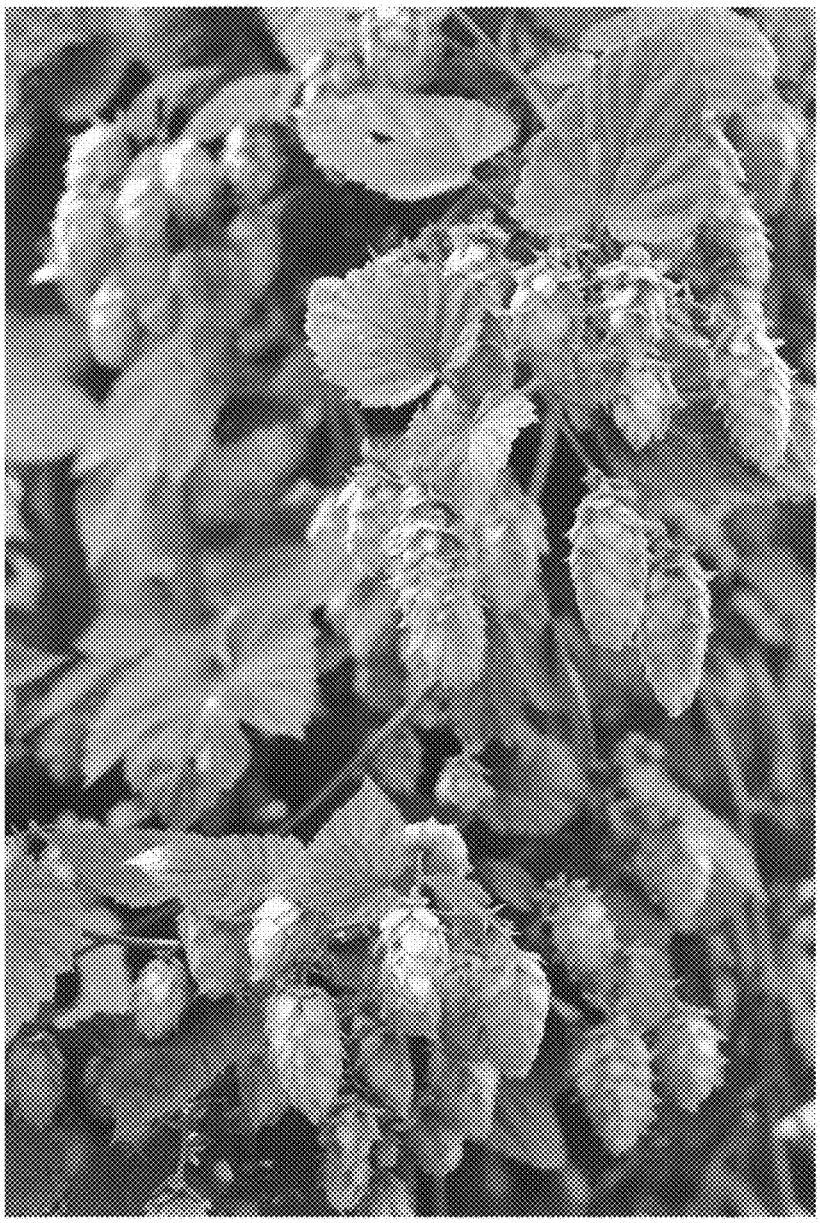
FIG. 2 illustrates cones and leaves of a mature 'ADHA 1940' hop plant.
Figure 3:
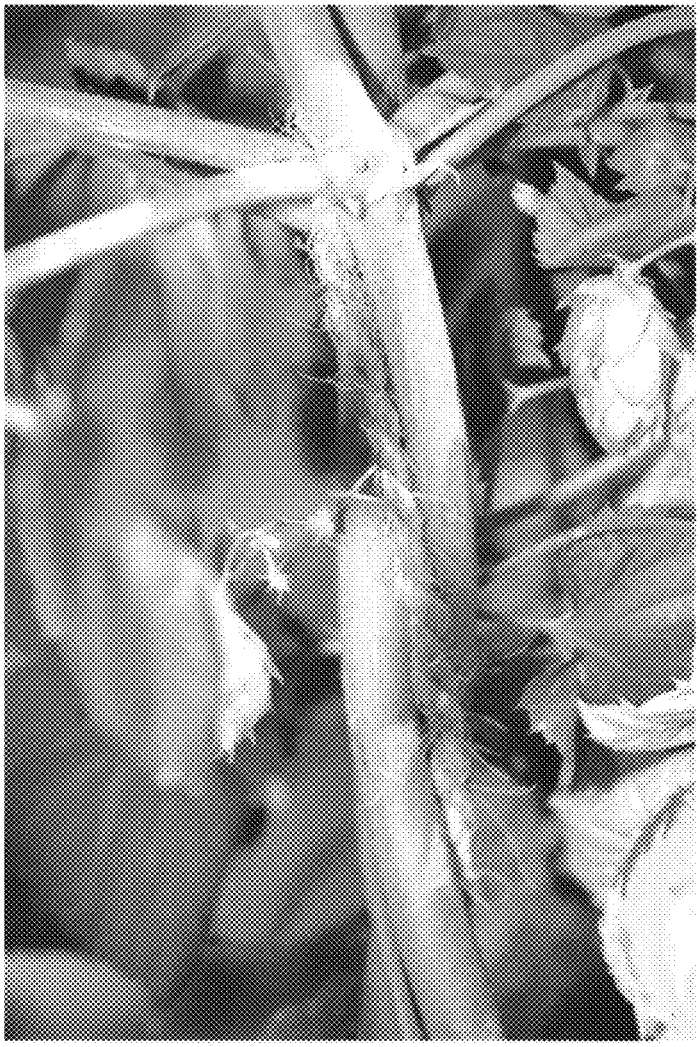
FIG. 3 illustrates a bine of a mature 'ADHA 1940' hop plant.
Figure 4:
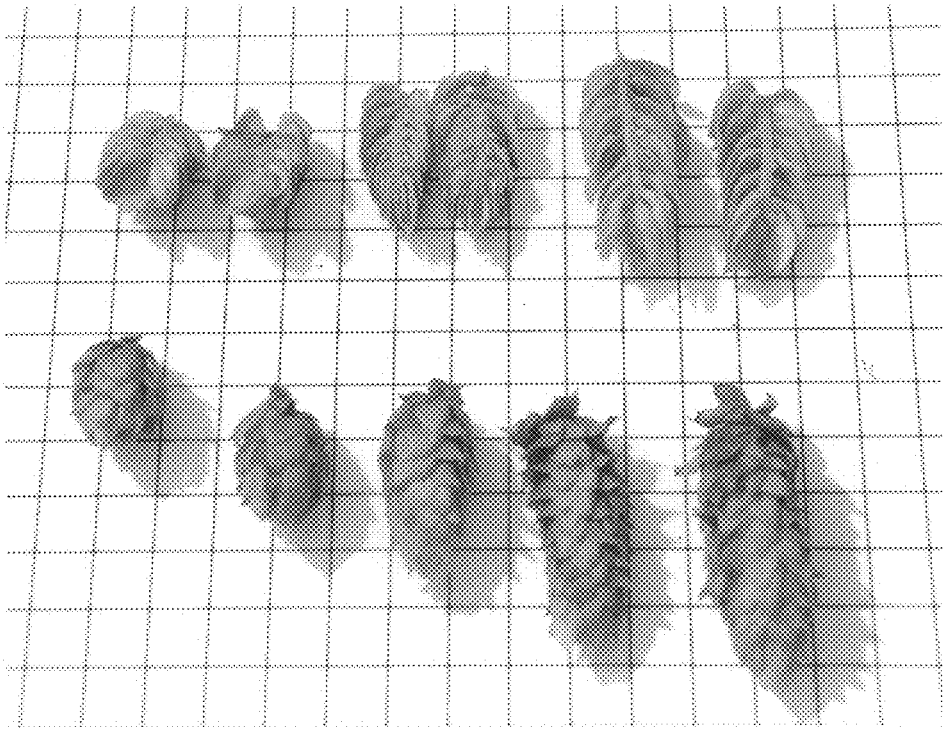
FIG. 4 illustrates whole cones and cross sections of cones of the 'ADHA 1940' hop plant.
Figure 5:
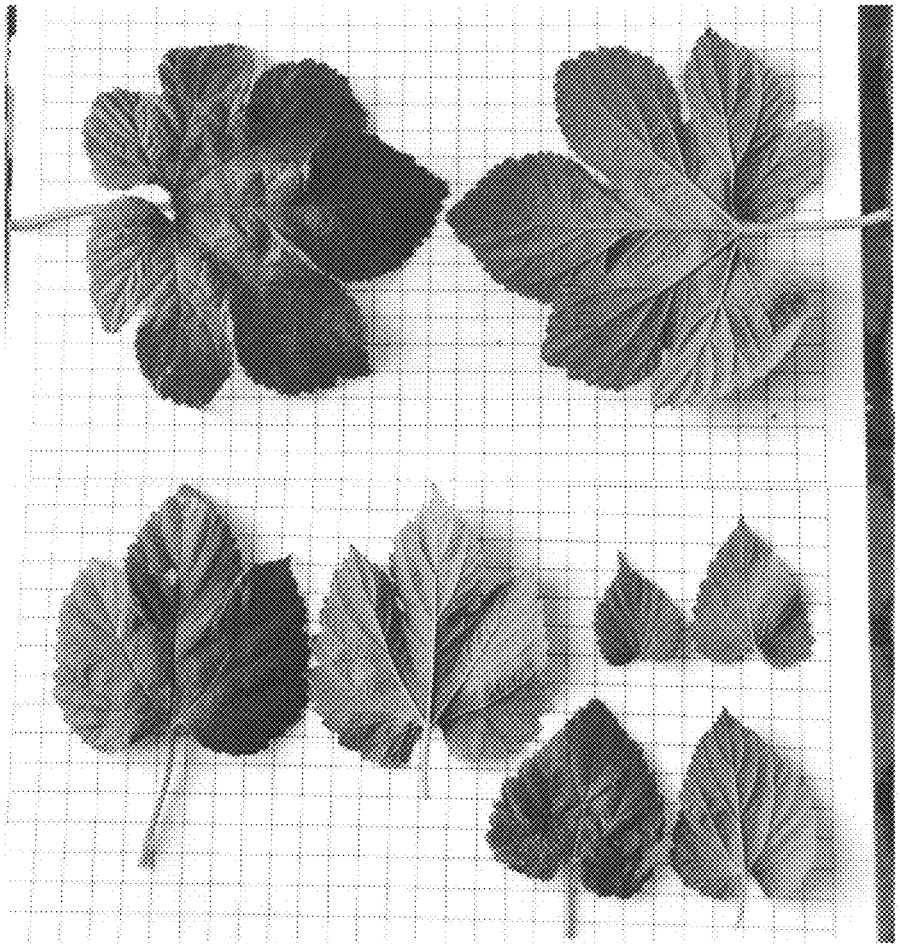
FIG. 5 illustrates leaves of a mature 'ADHA 1940' hop plant.

The colors of these illustrations may vary with lighting conditions and, therefore, color characteristics of this new variety should be determined with reference to the observations described herein, rather than from these illustrations alone.

COMPARISON OF 'ADHA 1940' TO PARENT PLANT AND COMARISON CULTIVAR

'ADHA 1940' is distinguishable from its parent plants, specifically its female parent 'Summit' (U.S. Plant Pat. No. 18,039), and unpatented male parent 'ADHA 34/95/57'. Table 1, below, sets forth some of the distinguishing characteristics of 'ADHA 1940' as compared to the 'Summit' cultivar, and to the 'Willamette' cultivar as a closely comparable cultivar:

TABLE 1

| Characteristic | 'ADHA 1940' | 'Summit' | 'Willamette' |
|---|---|---|---|
| Alpha Acid (α-Acids, % db) | 3.0-4.5 | 16-19 | 4.0-6.0 |
| Beta Acids (β-Fraction, % db) | 2.5-4.2 | 3-6 | 3.5-4.5 |
| Total Oil (ml/100 g) | 0.8-1.2 | 1.5-2.5 | 1.0-1.5 |
| Cohumulone (% of alpha acids) | 30-34 | 26-33 | 30-35 |

TABLE 1-continued

| Characteristic | 'ADHA 1940' | 'Summit' | 'Willamette' |
|---|---|---|---|
| Caryophyllene (% of total oil) | 12-22.5 | 6-10 | 7-8 |
| Farnesene (% of total oil) | 2-7 | <1 | 5-6 |
| Humulene (% of total oil) | 24-33 | 15-25 | 20-27 |
| Myrcene (% of total oil) | 40-55 | 30-50 | 30-40 |
| Aroma Profile | Aromatic; sweet, spicy, resinous, and floral | Aromatic; onion, garlic, grapefruit, tangerine, and earthy | Mild; slightly spicy |

DETAILED BOTANICAL DESCRIPTION

The following description is based on observations made during the 2018 growing season at Moxee, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color chart used was The Royal Horticultural Society Colour Chart, 4th ed., Copyright 2001, and all color observations were made outdoors in full sunlight.

Ploidy: Diploid.

Sex: Female.

Use: Brewing beer.

Harvest date: Late September (during the 2016-2019 growing seasons in Moxee, Wash.).

Time of flowering: Mid-July.

Plant type and shape: Climbing Bine, Normal (not Dwarf), and Cylindrical, when grown on a typical hop trellis.

Plant head shape: Approximate upper fifth of mature plant is Cylindrical, when grown on a typical hop trellis.

Observed disease and pest resistance or susceptibility:

*Powdery mildew* (*Podosphaera macularis*).—Moderately susceptible.

Hardiness: Observed Plant Hardiness Zone 6b.

Freeze tolerance: Typically intolerant of freezing temperatures during the growing season.

Bine:

*Color*.—Yellow Green Group 145A.

*Stripe*.—Not Present (anthocyanin coloration absent).

*Bine diameter*.—11 mm at base; 10 mm at 6 feet; and 1 mm at terminal end of approx. 18 ft.

*Stipule direction*.—Varied (forked upward, downward, and outward).

*Stipule color*.—Light Yellow Green Group 149A.

Laterals:

*Lateral length in upper third of plant*.—Considered medium in length.

*Number of cones per node on laterals in upper third of plant*.—Considered many.

*Lateral length in middle third of plant*.—Considered long in length, with dense foliage.

*Number of cones per node on laterals in middle third of plant*.—Considered many.

*Total number of cones on laterals*.—Considered many.

Leaf:

*Leaf arrangement*.—Opposite.

*Mature leaf shape*.—Palmately Lobed.

*Leaf apex shape*.—Cuspidate.

*Leaf base shape*.—Cordate.

*Color of mature leaf upper surface*.—Dark Green Group 136A.

*Color of mature leaf lower surface*.—Yellow Green Group 146A.

*Color of immature leaf upper surface*.—Green Group 137C.

*Color of immature leaf lower surface*.—Dark Green Group 144A.

*Average length of mature leaf*.—10 cm.

*Average width of mature leaf*.—13 cm.

*Number of lobes*.—3 to 7.

*Margin*.—Serrate.

*Serrations per inch*.—5 to 7.

*Venation pattern*.—Palmate.

*Blistering on mature upper leaves*.—Variable, typically very weak due to insect feeding.

Petiole:

*Average petiole length* (*mature*).—6.0 cm.

*Petiole average diameter*.—3.5 mm.

*Petiole color at base*.—Yellow Green Group 145A.

*Petiole color at terminal end*.—Yellow Green Group 145A.

Cone:

*Cone shape*.—Linear ovate or elongated ovate.

*Cone tip shape*.—Ovate.

*Cone average length*.—3.8 cm.

*Cone average width*.—1.7 cm.

*Cone average weight*.—0.46 g.

*Degree of opening*.—Slightly open.

*Pickability*.—Easy.

Bracts:

*Bract shape*.—Flared ovate — aristate.

*Bract tip shape*.—Caudate Bract, average length 1.5 cm.

*Bract average width*.—0.9 cm.

*Bract apex length*.—Long.

*Bract tip position*.—Flared.

*Bract tip color*.—Dark Green Group 144A.

*Bract middle color*.—Yellow Green Group 145A.

*Bract base color*.—Yellow Green Group 145A.

Bracteoles:

*Bracteole color*.—Yellow Green Group 145A.

*Bracteole average length*.—1.4 cm.

*Bracteole average width*.—0.7 cm.

*Bracteole shape*.—Elliptic.

*Bracteole compactness*.—Loosely compact.

Quality characteristics (averages):

*Alpha acid* (*as % of cone weight*).—3.0 to 4.5.

*Beta acid* (*as % of cone weight*).—2.5 to 4.2.

*Cohumulone* (*as % of alpha acids*).—28 to 32.

Analytical characteristics:

*Total oils* (*mg*/100 *g of cones*).—0.8 to 1.2.

*Humulene*.—24% to 33% of total oils.

*Caryophyllene*.—12% to 22.5% of total oils.

*Myrcene*.—28% to 31% of total oils.

*Farnesene*.—2% to 7% of total oils.

*Linalool*.—Less than 1% of total oils.

*Geranyl*.—Less than 1% of total oils.

*B-pinene*.—Less than 1% of total oils.

What is claimed:

1. A new and distinct variety of Hop plant named 'ADHA1940', substantially as illustrated and described herein.

* * * * *